United States Patent
Zou et al.

(10) Patent No.: US 11,702,627 B2
(45) Date of Patent: Jul. 18, 2023

(54) HIGH CAMP YIELDING YEAST STRAIN AND USE THEREOF

(71) Applicant: TIANJIN UNIVERSITY, Tianjin (CN)

(72) Inventors: Shaolan Zou, Tianjin (CN); Wenxuan Gao, Tianjin (CN); Yun Hu, Tianjin (CN); Shunhua Yang, Tianjin (CN); Pingsheng Ma, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 569 days.

(21) Appl. No.: 16/094,874

(22) PCT Filed: Feb. 18, 2016

(86) PCT No.: PCT/CN2016/074067
§ 371 (c)(1),
(2) Date: Oct. 18, 2018

(87) PCT Pub. No.: WO2017/139959
PCT Pub. Date: Aug. 24, 2017

(65) Prior Publication Data
US 2019/0390157 A1    Dec. 26, 2019

(51) Int. Cl.
*C12N 1/16*     (2006.01)
*C12N 1/14*     (2006.01)
*C12N 15/01*    (2006.01)
*C12R 1/645*    (2006.01)

(52) U.S. Cl.
CPC ............... *C12N 1/16* (2013.01); *C12N 15/01* (2013.01); *C12N 1/145* (2021.05); *C12N 2310/11* (2013.01); *C12N 2310/141* (2013.01); *C12N 2310/20* (2017.05); *C12R 2001/645* (2021.05)

(58) Field of Classification Search
CPC .......... C12N 1/16; C12N 15/01; C12N 1/145; C12N 2310/11; C12N 2310/141; C12N 2310/20; C12N 9/1205; C12R 2001/645; C12P 19/32; C07K 14/395
See application file for complete search history.

(56) References Cited

PUBLICATIONS

Livas et al. Transcriptional responses to glucose in *Saccharomyces cerevisiae* strains lacking a functional protein kinase A. 2011. BMC Genomics 12:405 (Year: 2011).*
Pinson et al. 2000. Redox regulation of AMP synthesis in yeast: a role of the Bas1p and Bas2p transcription factors. Molecular Microbiology 36(6), 1460-1469 (Year: 2000).*
Vandamme et al. Molecular mechanisms of feedback inhibition of protein kinase A on intracellular cAMP accumulation. 2012 Cellular Signaling 241610-1618 (Year: 2012).*
Tian et al. Dual Specificity and Novel Structural Folding of Yeast Phosphodiesterase-1 for Hydrolysis of Second Messengers Cyclic Adenosine and Guanosine 3',5'-Monophosphate. 2014. Biochemistry 2014, 53, 4938-4945 (Year: 2014).*
Brandeis Lecture. 2012. Fundamentals of Modern Genetic analysis. www.bio.brandeis.edu/classes/biol122a/Background.htm. (Year: 2012).*
Daniela Livas et al. "Transcription Responses to Glucose in *Saccharomyces cerevisiae* Strains Lacking a Functional Protein Kinase A", Journal of A, BMC Genomics, Aug. 9, 201 (Aug. 9, 2011), No. 405, vol. 12.

* cited by examiner

*Primary Examiner* — Samuel C Woolwine
*Assistant Examiner* — Tiffany Nicole Grooms
(74) *Attorney, Agent, or Firm* — Platinum Intellectual Property PC

(57) ABSTRACT

Provided is a yeast strain capable of excessively synthesizing cAMP and its construction method and fermentation technique thereof, and application in the field of medicine, animal husbandry, food or chemical industry. The yeast strain includes first and second gene modifications, wherein the first gene includes protein kinase A (PKA) catalytic subunit encoding genes TPK1, TPK2 and TPK3, by modifying the first gene, the activity or expression of PKA is completely inhibited, so that feedback inhibition to cyclic adenosine monophosphate (cAMP) is eliminated, but at the same time, the growth of the yeast is inhibited; and the second gene modification eliminates growth inhibition caused by the first gene modification, so that the yeast grows normally, and the cAMP yield by the yeast is increased, wherein the increase of the cAMP yield is relative to the cAMP yield by an unmodified yeast. The yeast strain further includes third and/or fourth gene modifications. The recombinant yeast strain of the present invention can stably, continuously and efficiently produce extracellular cAMP by up to 9721.6 μmol/L.

11 Claims, 3 Drawing Sheets
Specification includes a Sequence Listing.

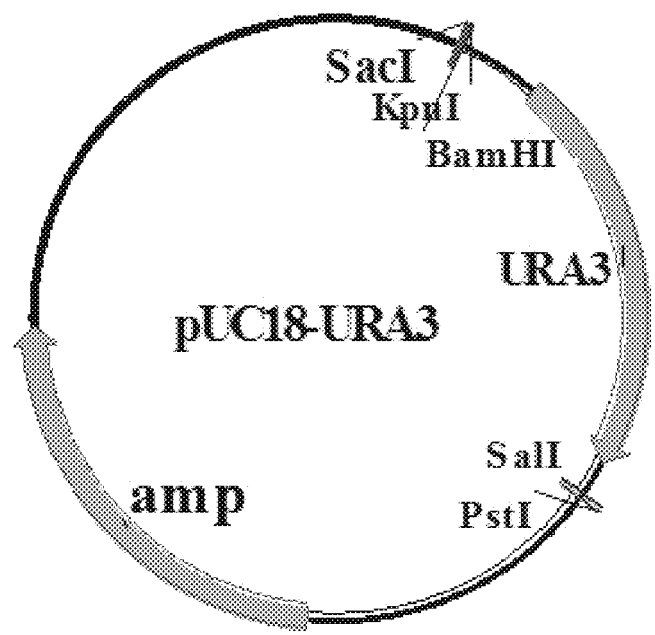
Fig. 1A
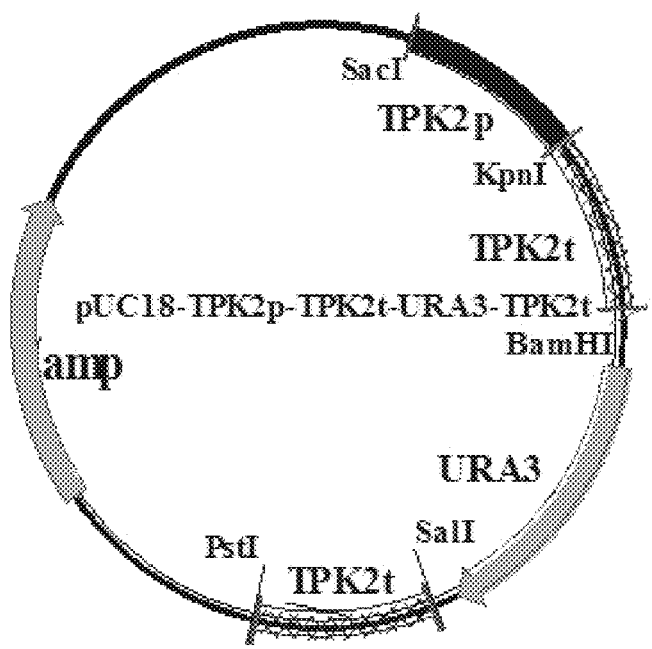
Fig. 1B
Fig. 1

HIGH CAMP YIELDING YEAST STRAIN AND USE THEREOF

RELATED APPLICATIONS

This application is a United States National Stage Application filed under 35 U.S.C. 371 of PCT Patent Application Serial No. PCT/CN2016/074067, filed Feb. 18, 2016, the disclosure of all of which are hereby incorporated by reference in their entirety.

INCORPORATION BY REFERENCE

Under 37 CFR 1.823, this application incorporates the Sequence Listing that was filed on Feb. 13, 2019 (file title: SUBSEQUENCELISTING_6101_0001_120190213; file size: 7,191 bytes) into the present disclosure.

TECHNICAL FIELD

The present invention belongs to the technical fields of genetic engineering and microbial fermentation, and particularly relates to a yeast strain capable of excessively synthesizing extracellular cAMP and a construction method and fermentation technique thereof, and an application of the yeast strain in the fields of medicine, animal husbandry, food or chemical industry.

BACKGROUND ART

Cyclic adenosine monophosphate (cAMP) is an important physiologically-active substance widely present in human body. As a second messenger in a cell, the cAMP plays an important regulatory role in sugar metabolism, fat metabolism, nucleic acid synthesis, protein synthesis and the like. At present, cAMP is widely used in medicine: clinically, cAMP is used for the treatment of angina pectoris, myocardial infarction, myocarditis, cardiogenic shock, etc.; cAMP has a certain effect on improving symptoms such as palpitations, shortness of breath and chest tightness in rheumatic heart disease; cAMP can improve the treatment efficacy for acute leukemia in combination with chemotherapy, and can also be used for remission induction of acute leukemia; and in addition, cAMP has a certain effect on chronic bronchitis in the elderly, various hepatitis and psoriasis. cAMP can also be used as a pharmaceutical intermediate to prepare dibutyryl cyclic adenosine monophosphate and meglumine cyclic adenylate so as to improve fat solubility and thereby exert more effective physiological and pharmacological function, cAMP can also be used as a food additive for livestock and poultry. It functions similar to growth hormone under ex vivo conditions the action of growth hormone under ex vivo condition and it can promote the growth of livestock and poultry and increase the yield of high-quality poultry products.

The method to produce cAMP includes chemical synthesis, enzymatic conversion and microbial fermentation. At present, all domestic and international industrial production uses chemical synthesis with adenosine-5'-monophosphate (AMP) as a raw material, the chemical synthesis uses a high-efficiency separation column for intermediate separation, and thus, is complex in operation and expensive in reagents involved, and the use of large amounts of pyridine as a solvent also causes serious environmental pollution. The enzymatic conversion uses adenylate cyclase (EC4.6.1.1, Cyr1p) as an enzyme source to catalyze ATP as raw material for one-step production of cAMP, however, this method has the shortcomings of an expensive substrate, a low content of adenylate cyclase, difficulty in purification, poor stability and the like, so the method is still limited to the laboratory stage and far from industrial application. In contrast, the microbial fermentation has the advantages of milder condition, simpler process, fewer by-products and lower environmental pollution, can utilize a cheap carbon source, realize continuous production, and is a potential technique that is worth developing.

At present, the production of cAMP by bacterial fermentation using *Brevibacterium liquefaciens, Microbacterium, Corynebacterium, Arthrobacter* and *Escherichia coli* has been studied, but the bacterial fermentation has the problems of poor repeatability, unstable yield, high cost, difficulty in industrialization and the like. Yeast, especially *Saccharomyces cerevisiae*, is one of the most important industrial microorganisms. It has the advantages of mature industrial application technology and strong stress resistance, and is a GRAS microorganism. As the first microbial strain to achieve whole genome sequencing, the yeast is one of the most important model organisms in molecular biology and genetics. The basic research related to cAMP signaling pathway and its regulation is deepened, and the genetic manipulation technology is perfect in approach. Unfortunately, current research at home and abroad has focused on the signaling regulation function of intracellular cAMP, and always ignored to study its extracellular production as a product. It is predicted that if extracellular cAMP production is also deeply investigated and fermentation process is developed with a yeast strain which is genetically modified to excessively produce extracellular cAMP, the cost will be greatly reduced and the technique will be simplified. Therefore, a new kind of microbial fermentation method will be established to promote green and clean production of high-value medicines and biochemical products, which will be proved to have an important economic and social significance.

SUMMARY

3.1 Brief Summary of the Invention

In order to overcome the deficiencies of the prior art mentioned above, the present invention provides a yeast strain which can be easily cultured, is more suitable for large-scale fermentation production and thus easier to be used in industrial application and can excessively synthesize extracellular cAMP by genetic modification, a recombination method to construct the strain and application of the strain.

The present invention provides a yeast strain subjected to first and second gene modifications, wherein the first gene includes protein kinase A (PKA) catalytic subunit encoding genes TPK1, TPK2 and TPK3; by modifying the first gene, the activity or expression of PKA is completely inhibited, so feedback inhibition to cAMP is eliminated, but at the same time, the growth of the yeast is inhibited; by modifying the second gene, growth inhibition caused by the first gene modification is eliminated, so the yeast grows normally, and the cAMP yield by the yeast is increased, wherein the increase of the cAMP yield is relative to the cAMP yield by the yeast not subjected to gene modification.

Preferably, the second gene includes, but is not limited to, protein kinase Rim15 encoding gene RIM15, transcription factor Msn1/Msn2 encoding gene MSN1/MSN2, protein kinase Yak1 encoding gene YAK1 or protein kinase Sch9 encoding gene SCH9, preferably YAK1. More preferably, the second gene modification enables the activity or expression of the modified gene codase to be completely inhibited, or enables activity increase or overexpression of the codase.

Preferably, the second gene modification enables the activity or expression of the protein kinase Rim15 encoding gene RIM15, transcription factor Msn1/Msn2 encoding gene MSN1/MSN2 or protein kinase Yak1 encoding gene YAK1 codase to be completely inhibited, or enables activity increase or overexpression of the protein kinase Sch9 encoding gene SCH9 codase.

Further, the above-mentioned yeast further includes a third gene modification to reduce the degradation of cAMP, thereby increasing cAMP yield.

Preferably, the third gene is cAMP phosphodiesterase encoding gene PDE1 and/or PDE2, preferably PDE1. More preferably, the third gene modification enables the activity or expression of the modified gene codase to be completely inhibited.

Preferably, the above-mentioned gene modification manner enabling the activity or expression of the codase to be completely inhibited includes point mutation, deletion, insertion, antisense polynucleotides, siRNA, microRNA or CRISPR, more preferably deletion and point mutation; and the gene modification manner enabling activity increase or overexpression of the codase includes point mutation, ligation of a strong promoter, ligation of an enhancer or increase of a copy number.

Further, the above-mentioned yeast further includes a fourth gene modification to enhance positive regulation of synthesis of a cAMP precursor in a purine synthesis pathway, so that the synthesis of the cAMP precursor increases, thereby increasing the cAMP yield.

Preferably, the fourth gene includes, but is not limited to, transcription factor Bas1 and Bas2 encoding genes. More preferably, the gene modification increases the expression of the Bas1/Bas2 complex.

Preferably, the above-mentioned fourth gene modification manner includes, but is not limited to, point mutation, ligation of a strong promoter, ligation of an enhancer, increase of a copy number or fusion co-expression, more preferably the fusion co-expression.

Further, the gene modification manner includes the use of a selectable marker gene. Preferably, the selectable marker gene includes, but is not limited to, URA3, LEU2, HIS3, TRP1 or LYS2. More preferably, the URA3 selectable marker gene is used. Further, more preferably, the gene modification manner is to recycle the selectable marker gene without retaining the selectable marker gene.

The yeast strain described in the present invention has higher extracellular cAMP yield than the yeast not subjected to first and second gene modifications, or the yeast not subjected to first, second and third gene modifications, or the yeast not subjected to first, second, third and fourth gene modifications. For example, the yeast strain described herein has an extracellular cAMP yield of up to 9721.6 μmol/L.

The yeast strain described in the present invention is any of *Saccharomyces cerevisiae. Saccharomyces pastorianus, Pichia stipitis, Saccharomyces Bayanus* and *Candida shehatae*, preferably *Saccharomyces cerevisiae*.

An object of the present invention is to provide a method for constructing the above-mentioned yeast strain capable of greatly increasing extracellular cAMP yield.

The first gene modification is firstly introduced into the yeast to eliminate the feedback inhibition to cAMP, but at the same time, the growth of the yeast is inhibited; and the second gene modification eliminates the growth inhibition caused by the first gene modification, so that the yeast grows normally.

Further, the method further includes performing the third gene modification on the yeast to reduce the degradation of cAMP, thereby further increasing the cAMP yield.

Furthermore, the method further includes performing the fourth gene modification on the yeast to enhance the positive regulation of synthesis of the cAMP precursor in the purine synthesis pathway, so that the synthesis of the cAMP precursor increases, thereby increasing the cAMP yield.

An object of the present invention is to provide a fermentation method for producing cAMP by using the above-mentioned yeast strain.

Further, the fermentation method includes fermentation medium components such as a carbon source, a nitrogen source and a trace element, and also includes temperature and rotation speed.

Preferably, in the fermentation method, the fermentation medium contains 20-150 g/L glucose, 10-20 g/L yeast extract and 20-40 g/L peptone, and the addition amount of adenine is 0-1.25 g/L.

An object of the present invention is to provide a fermentation broth produced by the fermentation of the above-mentioned yeast.

An object of the present invention is to provide application of any of the above-mentioned yeast strains or the fermentation broth in production of cAMP.

An object of the present invention is to provide application of any of the above-mentioned yeast strains or the fermentation broth in the fields of medicine, animal husbandry, food or chemical industry.

An object of the present invention is to provide application of any of the above-mentioned yeast strains or the fermentation broth in preparation of products in the fields of medicine, animal husbandry, food, chemical industry or the like.

Accordingly, the present invention further provides products containing any of the above-mentioned yeast strains or the fermentation broth in the fields of medicine, animal husbandry, food or chemical industry, such as drugs, feed, food and the like.

Unless otherwise stated, all technical terms and technical concepts referred to herein are well known to those skilled in the art. Although a variety of similar or equivalent methods can be used to construct and determine the yeast strains involved in the present invention, a suitable method and material will be described hereinafter. These materials, methods, and examples are illustrative only and are not intended to limit the invention to any degree. All documents, patents, and other references mentioned herein are subject to their integrity. The methods and materials to which the present invention pertains will be presented below in conjunction with the detailed description and the drawings.

3.2 Detailed Description

The present invention provides a genetically modified yeast strain capable of excessively synthesizing extracellular cAMP, a recombination method for constructing the strain and application of the strain. More particularly, As described above, the yeast of the present invention includes a first gene modification and a second gene modification. Further, the yeast further includes third and fourth gene modifications. The first gene modification eliminates feedback inhibition to cAMP, but at the same time, the growth of the yeast is inhibited; the second gene modification eliminates the growth inhibition caused by the first gene modification, so that the yeast grows normally; the third gene modification reduces the degradation of cAMP; and the fourth gene modification enhances positive regulation of synthesis of a cAMP precursor in a purine synthesis pathway, so that the synthesis of the cAMP precursor increases, thereby increasing the cAMP yield.

More particularly, the first gene modification enables the activity or expression of PKA to be completely inhibited by modifying the protein kinase A (PKA) catalytic subunit encoding genes TPK1, TPK2 and TPK3, so that the feedback inhibition to cAMP by PKA is eliminated, but at the same time, the growth of the yeast is inhibited; the second gene modification eliminates the growth inhibition caused by the first gene modification, so that the yeast grows normally; the second gene modification enables the activity or expression of protein kinase Yak1 and the like to be completely inhibited so as to eliminate cell growth inhibition caused by the complete inhibition to the activity or expression of PKA, so that the strain grows normally; the third gene modification enables the activity or expression of phosphodiesterase Pde for degrading cAMP to be completely inhibited; and the fourth gene modification enhances the positive regulation of synthesis of a cAMP precursor in the purine synthesis pathway, such as the activity or expression of transcription factors Bas1 and Bas2, so that the synthesis of the AMP increases, thereby finally increasing the cAMP yield.

The present invention describes the elimination of feedback inhibition to cAMP by PKA by the first and second gene modifications of the yeast strain to increase the extracellular cAMP yield. PKA is currently the only known cAMP target in yeast. It is generally believed that fluctuations in cAMP concentration exert effects through a PKA pathway; in other words, the intracellular cAMP signaling pathway is regulated by strict negative feedback of PKA. The yeast PKA is a tetrameric protein composed of two catalytic subunits and a dimeric regulatory subunit. PKA is present in the form of a passivated complex at the time of a lack or lower level of intracellular cAMP. When the intracellular cAMP level increases, cAMP is bound to the regulatory subunit of PKA, and the catalytic subunits of PKA are dissociated from the regulatory subunit to activate a series of protein phosphorylation cascade reactions, resulting in changes in the activity of these proteins, thereby regulating the level of the intracellular cAMP at different levels; a primary effector enzyme is adenylate cyclase Cyr1, and Cyr1 catalyzes the synthesis of cAMP from ATP. The regulatory subunit of PKA is encoded by the gene BCY1, and the catalytic subunits are encoded by the genes TPK1, TPK2 and TPK3.

When the activity or expression of the three catalytic subunits Tpk1, Tpk2 and Tpk3 are completely inhibited at the same time, the activity of PKA is completely inhibited, and the feedback inhibition to cAMP by PKA is eliminated. On the other hand, when the activity of PKA is completely inhibited, the protein kinase Rim15 stays in a nucleus and activates transcription factor Msn1/Msn2, and the Msn1/Msn2 further activates the protein kinase Yak1 which negatively regulates cell growth, so that the cells stay in the GI stage and cannot continue to grow. Therefore, the yeast strain of which the activity of PKA is completely inhibited requires further gene modification to ensure normal growth of the strain.

A protein kinase Sch9 has homology with the catalytic subunits of PKA, and the Sch9 and PKA have different substrates under normal physiological conditions; however, increasing the activity of either kinase compensates for growth defects caused by deletion of another kinase.

The first gene modification in the present invention eliminates the feedback inhibition to cAMP by PKA, so that the activity or expression of PKA is completely inhibited; and the second gene modification eliminates the growth inhibition of the yeast strain caused by the first gene modification, so that the yeast strain grows normally. There are different strategies for eliminating the feedback inhibition to cAMP by PKA and maintaining the normal growth of the strain under the condition that the activity of PKA is completely inhibited. The gene modification by which the activity or expression of PKA is completely inhibited and the feedback inhibition to cAMP by PKA is eliminated, can be carried out in a nucleic acid sequence of encoding catalytic subunits Tpk1, Tpk2 and Tpk3, and this nucleic acid sequence can be a regulatory region or a coding region.

The nucleic acid sequence of Tpk1 can be found, for example, in GenBank Accession No. NC_001142.9.

The nucleic acid sequence of Tpk2 can be found, for example, in GenBank Accession No. NC_001148.4.

The nucleic acid sequence of Tpk3 can be found, for example, in GenBank Accession No. NC_001143.9.

The strategy for maintaining the normal growth of the strain under the condition that the activity of PKA is completely inhibited includes, but is not limited to, performing gene modification on the protein kinase Rim15 encoding gene RIM15, transcription factor Msn1/Msn2 encoding gene MSN1/MSN2 or protein kinase Yak1 encoding gene YAK1, and as a result of the modification, the activity or expression of a corresponding enzyme is completely inhibited, and the strain can thus grow normally. The strategy for maintaining the normal growth of the strain under the condition that the activity of PKA is completely inhibited also includes, but is not limited to, performing gene modification on the protein kinase Sch9 encoding gene SCH9, and as a result of the modification, the activity or expression of a corresponding enzyme is increased, and the strain can thus grow normally.

The nucleic acid sequence of Yak1 can be found, for example, in GenBank Accession No. NC_001142.9.

The nucleic acid sequence of Rim15 can be found, for example, in GenBank Accession No. NC_001138.5.

The nucleic acid sequences of the Msn1/Msn2 can be found, for example, in GenBank Accession No. NC_001147.6 and NC_001145.3.

The nucleic acid sequence of Sch9 can be found, for example, in GenBank Accession No. NC_001140.6.

Regardless of the manner by which the first and second gene modifications result in complete inhibition of the activity or expression of enzyme or increased activity or expression of the enzyme, in the modification steps of four genes, namely TPK1, TPK2, TPK3 and a second gene in the yeast strain, except for the inactivation of a combination of TPK1, TPK2 and TPK3 in a haploid yeast cell (this combination cannot survive due to growth defects), the above-mentioned four genes may be modified in any order and in any combination.

The yeast strain subjected to the first and second gene modifications described above in the present invention produces more extracellular cAMP relative to the yeast strain not subjected to the first and second gene modifications.

On the other hand, once cAMP is produced, the only way to inactivate it is to hydrolyze it to 5'-AMP under the catalysis of cyclic nucleotide phosphodiesterase Pde. Therefore, Pde also affects the level of the intracellular cAMP. Thus, the third gene modification enables the activity or expression of the Pde to be completely inhibited, thereby reducing the degradation of cAMP and increasing the content level of cAMP. *Saccharomyces cerevisiae* cells themselves contain two cAMP phosphodiesterases: Pde1 encodes a low-affinity (Km=20-250 µM), low-specificity enzyme that primarily mediates rapid cAMP signaling; and Pde2 encodes a high-affinity (Km=170 nM), high-specificity enzyme that primarily controls the basal level of cAMP.

The nucleic acid sequence of Pde1 can be found, for example, in GenBank Accession No. NC_001139.9.

The nucleic acid sequence of Pde2 can be found, for example, in GenBank Accession No. NC_001147.6.

The first, second and third gene modifications described in the present invention can be realized by any of a variety of methods known in the art. The gene modification manner enabling the activity or expression of the codase to be completely inhibited can be performing point mutation, deletion or insertion of one or more nucleotides on the nucleic acid sequence of the gene, and the point mutation is, for example, conversion (purine to purine or pyrimidine to pyrimidine) or transversion (purine to pyrimidine or pyrimidine to purine) of mononucleotide. Mutations of a nucleic acid can result in the replacement of one or more conservative or non-conservative amino acids in the polypeptide it expresses. This replacement may result in a change in the conformation of the polypeptide, or loss of some or all of its functions. A frameshift mutation may occur, which will result in the entire polypeptide chain to encode a completely different polypeptide from this point, or a stop codon may be formed in advance to make the polypeptide chain defective or even silence the gene.

The nucleic acid sequence for deletion or insertion can be obtained by PCR or chemical synthesis, or can be obtained by cell replication amplification. The gene modification enabling the activity or expression of the enzyme of the gene to be completely inhibited can also be realized by providing or expressing antisense polynucleotides, siRNA, microRNA or other nucleic acids capable of preventing mRNA of the gene to be modified from being translated into protein. Transcription activator-like effector nuclease (TALEN) and CRISPR (Clustered Regularly Interspaced Short Palindromic Repeats) developed in recent years can also be used to inactivate genes.

The gene modification that enables the activity or expression of the enzyme of the gene to be completely inhibited in the present invention means that the activity of the enzyme/polypeptide can be reduced (compared to an unmodified yeast or a wild-type yeast) by at least 95% (for example, at least 96%, 97%, 98%, 99% or 100%).

The gene modification manner enabling the activity increase or overexpression of the codase includes, but is not limited to, point mutation, ligation of a strong promoter, ligation of an enhancer, and increase of a copy number, for example, the point mutation to increase the activity of the polypeptide; increase of the copy number of the nucleic acid sequence; ligation of the nucleic acid sequence to an expressible strong promoter or enhancer by gene modification; change of the promoter of the nucleic acid sequence or other regulatory factors to increase its expression level (for example, increasing the binding strength of a promoter sequence and a transcription initiation factor); increase of the half-life of mRNA transcribed by the nucleic acid sequence; and inhibition to the degradation of the mRNA or polypeptide chain.

The gene modification that enables the increase of the activity or expression of the enzyme of the gene in the present invention means that the activity of the enzyme/polypeptide encoded by the nucleic acid sequence subjected to gene modification or the efficiency of action on a substrate is increased by at least 20% compared to a wild type. (for example, at least 25%, 30%, 40%, 50%, 60%, 70%, 80%, 90%, 95%, 99%, 100% or higher).

The yeast strain subjected to the above-mentioned first, second and third gene modifications produces more extracellular cAMP than the yeast strain not subjected to the first, second and third gene modifications, and even produces more extracellular cAMP than the yeast strain subjected to the first and second modifications.

The increase of the extracellular cAMP level of yeast cells can also be realized by regulating a purine synthesis pathway and increasing a synthesis amount of the cAMP synthesis precursor AMP in addition to by performing gene modification on the cAMP-PKA signaling pathway. In the purine synthesis pathway of *Saccharomyces cerevisiae*, the expression of the AMP de novo synthesis pathway gene, namely ADE gene, is positively regulated by the synergy between the 2 transcriptional regulators Bas1 and Bas2. Bas1 is a Myb transcriptional regulator, and Bas2, also known as Pho2, is a homeodomain transcriptional regulator; and Bas1 and Bas2 are bound to a specific promoter region in a complex form and synergistically activate the expression of 10 ADE genes. When the concentration of intracellular ADP and ATP is too high, ADP and ATP feedback-inhibit the activity of the first enzyme Ade4p (PRPP amide transferase, abbreviated as PRPPAT) in the de novo synthesis pathway, so that the synthesis of the intermediate product SAICAR decreases. Bas2p can sense the concentration change of SAICAR, and when this concentration decreases to a certain extent, Bas2p no longer forms a complex with Bas1p. When a considerable amount of adenine is present in the medium, the adenine enters the cell, AMP is formed through a salvage pathway, and the AMP is further converted into ADP and ATP, which also leads to inhibition to the synthesis of the entire de novo synthesis pathway.

The fourth gene modification increases the synthesis of the AMP by enhancing the positive regulation of synthesis of AMP in the purine synthesis pathway, thereby increasing the cAMP yield. The core of enhancing the positive regulation of AMP synthesis is to promote the formation of the Bas1/Bas2 complex, increase the positive regulation activity of the complex, and inhibit the feedback inhibition of adenine, ADP and ATP. There are a variety of strategies to promote the formation of the Bas1/Bas2 complex and increase the positive regulation activity of the complex: the activity or expression of a single positive regulation transcription factor Bas1 or Bas2 may be increased, or Bas1 and Bas2 are directly subjected to fusion co-expression, or the activity or expression level is further increased on the basis of the fusion co-expression of Bas1 and Bas2. There are a number of ways to increase the activity of a polypeptide encoded by a nucleic acid, for example, the point mutation to increase the activity of the polypeptide; increase of the copy number of the nucleic acid sequence; ligation of the nucleic acid sequence to an expressible strong promoter or enhancer by gene modification; change of the promoter of the nucleic acid sequence or other regulatory factors to increase its expression level (for example, increasing the binding strength of a promoter sequence and a transcription initiation factor; increase of the half-life of mRNA transcribed by the nucleic acid sequence; and inhibition to the degradation of the mRNA or polypeptide chain. It is believed that an increase in the activity of a polypeptide encoded by a nucleic acid sequence subjected to gene modification requires an increase in the efficiency of its action on the substrate by at least 20% (for example, at least 25%, 30%, 40%, 50%, 60%, 70%, 80%, 90%, 95%, 99%, 100% or higher) as compared to the wild type. Overexpression of a single copy or multiple copies of a nucleic acid sequence can be achieved by ligation into a vector or by integration into the genome of the yeast. Vectors suitable for overexpression of nucleic acid sequences have been commercialized or can be obtained by gene recombination techniques commonly used in the art. There have been some methods in the art for integrating nucleic acid sequences in a yeast genome. For example, Methods in Enzymology: Guide to Yeast Genetics and Molecular and cell Biology, Vol. 194, 2004, Abelson et al., eds., Academic Press. The vector containing the nucleic acid sequence can operably ligate some elements necessary for expression to a target nucleic acid sequence: a nucleic acid sequence expressing a selectable marker (such as an auxotrophic selectable marker gene, an antibiotic resistance gene) may be carried; or a gene (such as, 6×His tag) that can be used to purify a polypeptide may be carried; or one or more origins of replication may be carried. The elements necessary for expression include nucleic acid sequences capable of directing or regulating a target nucleic acid sequence, such as a promoter sequence. Representative promoters include (but are not limited to) the PGK promoter, the TPI1 promoter, and the ADH1 promoter. The elements necessary for expression also include an enhancer sequence, a response element, or an inducing factor that regulates expression of the coding sequence.

The elements necessary for expression may be from bacteria, yeasts, insects, plants, mammals, fungi or viruses, and an expression vector may carry elements from different sources. For the elements necessary for expression, see in Goeddel, 1990, Gene Expression Technology: Methods in Enzymology, 185, Academic Press, San Diego, Calif. In some cases, the most appropriate nucleic acid sequence for a particular codon or the element necessary for expression can be selected for obtaining best expression in a yeast cell. See Bennetzen & Hall, 1982, J. Biol. Chem., 257:3026-31.

The nucleic acid sequence of Bas1 can be found, for example, in GenBank Accession No. NC_001143.9.

The nucleic acid sequence of Bas2 can be found, for example, in GenBank Accession No. NC_001136.10.

The yeast strain subjected to the above-mentioned first, second, third and fourth gene modifications produces more extracellular cAMP than the yeast strain not subjected to the first, second, third and fourth gene modifications, and even produces more extracellular cAMP than the yeast strain subjected to the first, second modifications or the yeast strain subjected to the first, second, and third modifications.

In the gene modification process of the present invention, a nucleic acid sequence (e.g., an expression vector) can be introduced into a yeast cell or other host cells by a variety of methods. These methods include (but are not limited to) electroporation, calcium phosphate precipitation, heat shock, lipofection, microinjection, lithium chloride, lithium acetate, mercaptoethanol, and viral-mediated gene transfer.

In addition to yeast cells, the "host cells" can be any cell that can be used in standard molecular biology operations to produce nucleic acids and polypeptides, including, but not limited to, bacterial cells (such as *E. coli*), insect cells, plant cells, and mammalian cells (such as CHO or COS cells). The "Yeast cells" include the recombinant yeast cells described herein. The "host cells" as referred to herein include not only mother cells to which nucleic acid is transduced, but also daughter cells thereof.

In the gene modification process of the present invention, selectable marker genes for use in screening for transfer to yeast cells include, but are not limited to, any auxotrophic genes available for yeast, such as URA3, LEU2, HIS3, TRP1 and LYS2. In order to be able to perform as many gene modifications as possible while avoiding possible interference caused by auxotrophic gene expression itself, a URA3 gene which can be conveniently and repeatedly used is preferably used. Further more preferably, the URA3 gene is recycled without remaining in the genetically modified strain.

Although the strategy applied by the present invention targets the genes and polypeptides of the *S. cerevisiae* strain, the same strategy is also applicable to other fermentable yeasts, preferably yeast strains capable of industrial fermentation. In addition to the *S. cerevisiae* strain, suitable strains also include *Saccharomyces pastorianus, Pichia stipitis, Saccharomyces Bayanus* and *Candida shehatae*. The pathways or gene names may be slightly different for these strains, but the same strategies and techniques can be applied to modify corresponding pathways and homologous genes. The genetically engineered yeast strains described herein are well known to those skilled in the art.

The present invention also describes a fermentation method for producing cAMP by using the above-mentioned genetically modified yeast strain.

Preferably, in the fermentation method, the fermentation medium contains 20-150 g/L glucose, 10-20 g/L yeast extract and 20-40 g/L peptone, and the addition amount of adenine is 0-1.25 g/L.

The invention also describes application of the above-mentioned genetically modified yeast strain, which can be used to ferment metabolic carbohydrates to produce extracellular cAMP. Further, the above-mentioned genetically modified yeast strain cells, and/or fermented fermentation broth containing extracellular cAMP can directly be used as a substitute for cAMP, and is applied like cAMP to various fields, for example, medicine, animal husbandry, food or chemical industry, etc. Furthermore, the application includes application in the preparation of products in the above fields, such as pharmaceuticals, food, feed, and the like. Correspondingly, the present invention further provides a product comprising the above-mentioned genetically modified yeast strain cells and/or fermented fermentation broth containing extracellular cAMP in the fields of medicine, animal husbandry, food or chemical industry, such as pharmaceuticals, food, feed, etc.

3.3 Advantages and Benefits of the Invention

The recombinant yeast strain obtained by the invention has low nutrient requirement, can be easily cultured, is suitable for large-scale fermentation production and easy for realizing industrialization; by performing related gene modifications through genetic engineering, the metabolic flux to the cAMP precursor AMP is increased while eliminating cAMP pathway feedback inhibition and reducing cAMP degradation, so that the obtained recombinant yeast strain can stably, continuously and efficiently produce extracellular cAMP; and by increasing the carbon source concentration, optimizing the carbon/nitrogen ratio and adding the precursor and so on, the metabolic flux can be made to flow more efficiently to a target product, and an optimized high-yield extracellular cAMP fermentation technique can be obtained, with the cAMP concentration reaching 9721.6 μmol/L. The present invention overcomes the defects of complex technique, expensive raw materials, too many byproducts and severe environmental pollution in the traditional chemical synthesis, and also overcomes the defects of expensive substrate, poor stability of adenylate cyclase and the like in the enzymatic conversion. The present invention has the advantages of simple operation process, easy separation and extraction of products, low raw material cost, high safety and environmental protection, and industrialized production, opens up a new way for production of cAMP by microbial fermentation, and thus will promote green clean production of high-value medicines and biochemical products, can be widely used in the fields of medicine, animal husbandry, food or chemical industry, and therefore, has important economic and social significance.

BRIEF DESCRIPTION OF THE DRAWINGS

FIG. 1 is a schematic diagram of the plasmid according to Example 1, wherein FIG. 1A is the plasmid pUC18-URA3, and FIG. 1B is the plasmid pUC18-TPK2p-TPK2t-URA3-TPK2t.

DETAILED DESCRIPTION

Figure 2:
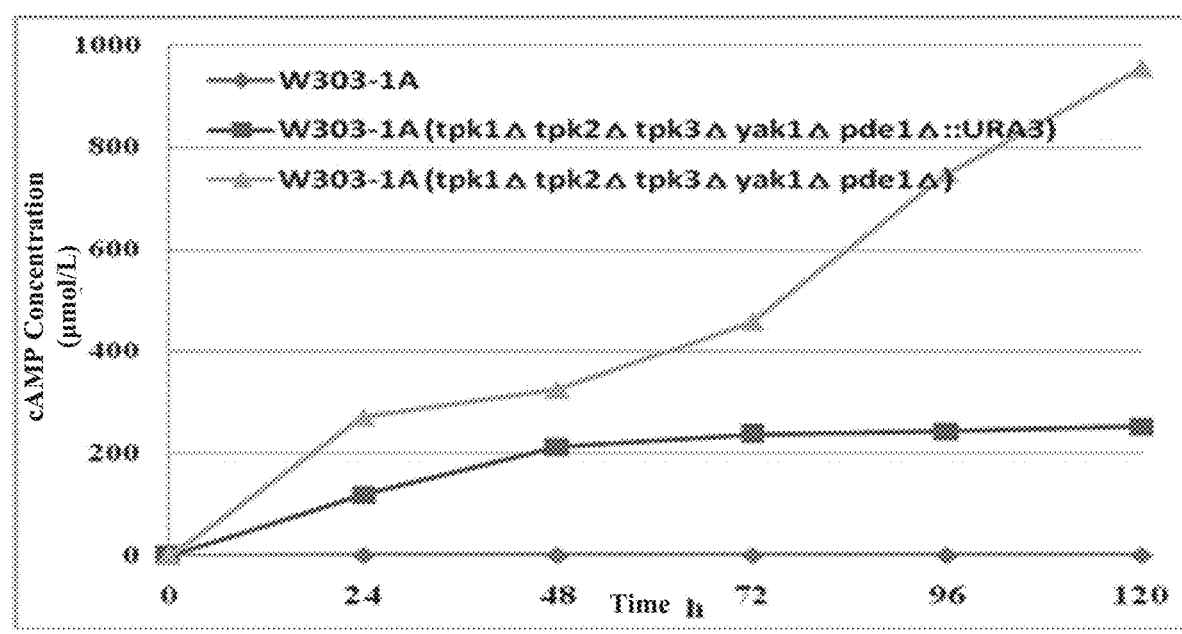
FIG. 2 is a preliminary evaluation of cAMP production of 5 gene deletion strains according to example 5.

The technical solution of the present invention will be further described below in conjunction with specific examples. It is understood that the specific implementations described herein are shown by way of examples, and are not intended to limit the invention. Unless otherwise specified, the technical means used in the examples are conventional means well known to those skilled in the art. The main features of the present invention can be applied to various implementations without departing from the scope of the invention. Those skilled in the art will recognize or be able to recognize that many equivalents can be used in the specific steps described herein by only using normal experiments. These equivalents are considered to be within the scope of the invention and are covered by the claims.

Several media involved in the examples are as follows:
1) Medium YPAD for Yeast Strain Activation and Seed Broth Preparation Yeast extract 10 g/L, peptone 20 g/L, glucose 20 g/L, and adenine 0.05 g/L, natural pH; agar powder 15 g/L is added in a case of solid media.

2) Transformation Screening Medium CMG-URA when Using Uracil (URA) Auxotrophic Selectable Marker Screening was performed using a uracil-free minimal medium CMG plate, CMG$^{-URA}$ plate for short. The components are as follows: amino acid-base mixture, 0.83 g/L; amino acid-free yeast nitrogen base, YNB for short, 6.7 g/L; glucose, 20 g/L; and agar powder, 15 g/L. The amino acid-base mixture therein is shown in Table 1.

TABLE 1

| Components of amino acid - base mixture | | | |
|---|---|---|---|
| Adenine 50 mg/L | Leucine 100 mg/L | Arginine 20 mg/L | Lysine 30 mg/L |
| Aspartic acid 100 mg/L | Methionine 20 mg/L | Glutamic acid 100 mg/L | Phenylalanine 50 mg/L |
| Histidine 100 mg/L | Serine 150 mg/L | Isoleucine 30 mg/L | Threonine 15 0 mg/L |
| Tryptophan 100 mg/L | Tyrosine 30 mg/L | Uracil 50 mg/L | Valine 150 mg/L |

Note: A selective medium can be made by eliminating specific amino acid components. The pH was adjusted to 5.6, the glucose was sterilized at 110° C. for 15 min, the other components were sterilized at 121° C. for 21 min, and all the components were mixed before use.

3) 5'-FOA Plate (5'-Fluoroorotic Acid Plate)
The preparation method is as follows:
a. 100 ml of 5'-FOA solution was prepared, including:
YNB w/o AA: 1.4 g dropout powder: 0.17 g 5'-FOA: 0.2 g
Uracil: 20 mg Adenine: 10 mg Leucine: 40 mg
Histidine: 30 mg Tryptophan: 20 mg Glucose: 4 g
All the components were dissolved by continuous stirring at 45° C. with a magnetic stirrer, followed by filtration sterilization;
b. 100 ml of agar powder Agar solution was prepared to a final concentration of 3.0%, sterilized at 121° C. for 15 min, and then cooled to 45° C.; and
c. 100 ml of 5'-FOA was uniformly mixed with 100 ml of Agar solution to prevent air bubbles from forming, and the mixture was poured into a sterile Petri dish, and cooled to form.

4) LB Medium for *E. coli* Culture
Yeast extract 5 g/L, peptone 10 g/L, and sodium chloride (NaCl) 10 g/L, pH adjusted to 7.0; agar powder 15 g/L is added in a case of solid media. Antibiotics are added as needed, and the final concentration of ampicillin is 100 μg/mL.

The primer sequences involved in the examples are shown in Table 2.

TABLE 2

Primer sequences used in the examples

| Sequence No. | Name | Sequence (5'→3') and Added Restriction Enzyme Cutting Sites |
|---|---|---|
| SEQ ID No. 1 | P1 | CCCGGGGGATCCTTGATICGGIAATCTCCGAA (BamHI) |
| SEQ ID No. 2 | P2 | CCCGGGGTCGACCTGAFATAATTAAATTGAAGCT (SalI) |
| SEQ ID No. 3 | P3 | CCCGGGGTCGACGGTACCACCTAACGGATGCCTTATTT (SalI KpnI) |
| SEQ ID No. 4 | P4 | CCCGGGCTGCAGGGATCCGGGATTTTGGACCTTAGACT (PstI BamHI) |
| SEQ ID No. 5 | P5 | CCCGGGGAGCTCTCAATTTGGTTGTAAGCAAC (SacI) |
| SEQ ID No. 6 | P6 | CCCGGGGGTACCCGACAATTTTCAACAGTATG (KpnI) |
| SEQ ID No. 7 | P7 | CCTCAAGATAAACCAGCTGG |
| SEQ ID No. 8 | P8 | ATAATGGTGATATCAGCACC |
| SEQ ID No. 9 | P9 | CCCGGGGTCGACGGTACCGTTACTACGGAGATGGAACG (SalI KpnI) |
| SEQ ID No. 10 | P10 | CCCGGGCTGCAGGGATCCATCCCTGAAGGCTTAAATAG (PstI BamHI) |
| SEQ ID No. 11 | P11 | CCCGGGGAGCTCCTCCGTTAATCCTAGTCTGT (SacI) |
| SEQ ID No. 12 | P12 | CCCGGGGGTACCTTCTGTGCTACCTTTGAAGC (KpnI) |
| SEQ ID No. 13 | P13 | ATCCCTCCCATCCTCCTTAA |
| SEQ ID No. 14 | P14 | GAAGGAGCCGCAGCATTATT |
| SEQ ID No. 15 | P15 | CCCGGGGTCGACGGTACCGATTCTTGGTGAGTCTAACA (SalI KpnI) |
| SEQ ID No. 16 | P16 | CCCGGGCTGCAGGGGATCCTGGAACGCTTTTTTGCTTGT (PstI BamHI) |
| SEQ ID No. 17 | P17 | CCCGGGGAGCTCGTCAACGTTTCAGATACTCT (SacI) |
| SEQ ID No. 18 | P18 | CCCGGGGGTACCTTTGTGCAGGCTCGTCTTT (KpnI) |
| SEQ ID No. 19 | P19 | GCGACTATGCATTTTTGCAAA |
| SEQ ID No. 20 | P20 | CGGAGCCTTCATGAGATAAA |
| SEQ ID No. 21 | P21 | CCCGGGGTCGACGGTACCAAAGTTTCTGCACTAGCTTT (SalI KpnI) |
| SEQ ID No. 22 | P22 | CCCGGGCTGCAGGGATCCAGAGAGAGGACCCATGGAAT (PstI BamHI) |
| SEQ ID No. 23 | P23 | CCCGGGGAGCTCCTTTCGCCCTCAAACTCAAC (SacI) |
| SEQ ID No. 24 | P24 | CCCGGGGGTACCATGTTCCCITGCACAATGGC (KPnI) |
| SEQ ID No. 25 | P25 | CAATACGGATGAATATTTGTG |
| SEQ ID No. 26 | P26 | ACTTTTGATTGCGCTGTGAA |
| SEQ ID No. 27 | P27 | CCCGGGGTCGACGGTACCAAATTCATTACCCGGGAGCA (salI KpnI) |
| SEQ ID No. 28 | P28 | CCCGGGCTGCAGGGATCCATGCTGGAACCCTCATATGA (PstI BamHI) |
| SEQ ID No. 29 | P29 | CCCGGGGAGCTCCAGACATATAGTCTCGAAGA (SacI) |
| SEQ ID No. 30 | P30 | CCCGGGGGTACCCCTCGTTAAAAGCCACTTTC (KpnI) |
| SEQ ID No. 31 | P31 | AATCTTACTTTGGCGAATG |
| SEQ ID No. 32 | P32 | ACACTATTTCCTTGTTCATAC |
| SEQ ID No. 33 | P33 | GCGCGCGAATTCCGTATTGACCATTCCTAA (EcoRI) |

TABLE 2-continued

Primer sequences used in the examples

| Sequence No. | Name | Sequence (5'→3') and Added Restriction Enzyme Cutting Sites |
|---|---|---|
| SEQ ID No. 34 | P34 | TCGACTCCCGGGTACC<u>GAGCTC</u>TATCGTATCGCAGCCTA (SacI) |
| SEQ ID No. 35 | P35 | GCTCGGTACCCGGGA<u>GTCGAC</u>TGTAGACCTAAGTTCAT (SalI) |
| SEQ ID No. 36 | P36 | ATATTA<u>GGATCC</u>GCCTTGCTTACCTAGATG (BamHI) |
| SEQ ID No. 37 | P37 | GCGTTA<u>GGATCC</u>GATTCGGTAATCTCCG (BamHI) |
| SEQ ID No. 38 | P38 | AGGTCTACAGGGGTAATAACTGATAT |
| SEQ ID No. 39 | P39 | GTTATTACCCCTGTAGACCTAAGTTCAT |
| SEQ ID No. 40 | P40 | CGTACG<u>AAGCTT</u>GCCTTGCTTACCTAGATG (HindIII) |
| SEQ ID No. 41 | P41 | GGGCCC<u>GAGCTC</u>TCTTTAGCCGTAATTGCGAA (SacI) |
| SEQ ID No. 42 | P42 | GTACGAGAATTCTTCCATCATGGATGTAGTCCTTGATATCTC |
| SEQ ID No. 43 | P43 | ATGATGGAAGAATTCTCGTAC |
| SEQ ID No. 44 | P44 | GGGCCC<u>GTCGAC</u>TCATATCCATCTATGCTCGTC (SalI) |
| SEQ ID No. 45 | P45 | TCAACTTTGGGATTACTGC |
| SEQ ID No. 46 | P46 | CTCATCATTTGCGTCATCT |

In the examples, the *S. cerevisiae* strain W303-1A (=ATCC208352) is commercially available from ATCC, USA. YCplac33 is available from Invitrogen. pUC18 is available from companies such as Invitrogen and Promega.

Example 1: Construction of TPK2 Gene-Deleted Yeast Strain

Using the homologous recombination double-exchange mechanism to delete the TPK2 gene on the yeast chromosome, the plasmid pUC18-TPK2p-TPK2t-UR43-TPK2t for deletion was firstly constructed. This plasmid was digested to be linearized and transformed into yeast competent cells, and URA3 was used as a selectable marker gene for screening to obtain the yeast strain tpk2Δ::URA3 obtained by double-exchange using TPK2p and TPK2t downstream of URA3 as the left and right homology arms, respectively; and the 5'-FOA plate was used for screening to obtain the yeast strain tpk2Δ in which the URA3 gene was ejected due to the recombination between two TPK2t sequences on the left and right sides of the URA3 in the tpk2Δ::URA3 chromosome.

The primers for construction and identification are shown in Table 2, and the schematic diagram is shown in FIG. 1.

I. Construction of pUC18-TPK2p-TPK2t-URA3-TPK2t

The construction of this plasmid involves four ligations:

(1) Construction of pUC18-URA3

The URA3 gene was amplified by PCR using plasmid YCplac33 as a template, the sequences shown in SEQ ID No. 1 and SEQ ID No. 2 in Table 2 were used as the forward and reverse primers P1 and P2, and the Fast Pfu polymerase produced by TransGen was used. The condition was annealed at 50° C. for 1 min and extended at 72° C. for 1.5 min for a total of 32 cycles to obtain a 1055 bp PCR fragment. This fragment and the vector plasmid pUC18 were digested by restriction enzymes BamHI and SalI, ligated by a T4 DNA ligase and transformed into *E. coli* Top 10 competent cells. The transformant plasmid was extracted and identified by restriction enzyme analysis to prove to obtain the target plasmid pUC18-BamHI-URA3-SalI (abbreviated as pUC18-URA3, see FIG. 1A).

(2) Construction of pUC18-TPK2t-URA3

The strain W303-1A chromosome was extracted and used as a template to amplify the terminator region of TPK2 gene (abbreviated as TPK2t) by PCR method. The sequences shown in SEQ ID No. 3 and SEQ ID No. 4 in Table 2 were used as the forward and reverse primers P3 and P4, the Fast Pfu polymerase produced by TransGen was used, and the condition was annealed at 50° C. for 1 min and extended at 72° C. for 0.5 min for a total of 32 cycles to obtain a 526 bp PCR fragment. This fragment and the vector plasmid pUC18-URA3 were digested by restriction enzymes KpnI and BamHI, ligated by a T4 DNA ligase and transformed into *E. coli* Top 10 competent cells. The transformant plasmid was extracted and identified by restriction enzyme analysis to prove to obtain the target plasmid pUC18-TPK2t-URA3.

(3) Construction of pUC18-TPK2p-TPK2t-URA3

The strain W303-1A chromosome was extracted and used as a template to amplify the promoter region of TPK2 gene (abbreviated as TPK2p). The sequences shown in SEQ ID No. 5 and SEQ ID No. 6 in Table 2 were used as the forward and reverse primers P5 and P6, the Fast Pfu polymerase produced by TransGen was used and the condition was annealed at 50° C. for 1 min and extended at 72° C. for 0.5 min for a total of 32 cycles to obtain a 532 bp PCR fragment. This fragment and the vector plasmid pUC18-TPK2t-URA3 were digested by restriction enzymes Sac I and Kpn I, ligated by a T4 DNA ligase and transformed into *E. coli* Top 10 competent cells. The transformant plasmid was extracted and identified by restriction enzyme analysis to prove to obtain the target plasmid pUC18-TPK2p-TPK2t-URA3.

(4) Construction of pUC18-TPK2p-TPK2t-URA3-TPK2t

The PCR product containing the TPK2t sequence amplified in the above (2) was digested with Sal I and Pst I, and ligated with the same double-digested pUC18-TPK2p-

TPK2t-URA3 large fragment to obtain the plasmid pUC18-TPK2p-TPK2t-URA3-TPK2t (see FIG. 1B).

II. Construction of W303-1A (tpk2Δ) Strain

The plasmid pUC18-TPK2p-TPK2t-URA3-TPK2t was digested with Sac I and Pst I to obtain a linearized DNA fragment TPK2p-TPK2t-URA3-TPK2t; and W303-1A strain competent cells were transformed with this linearized fragment by a lithium acetate method, a uracil auxotrophic selectable marker (URA3) was used for screening, that is, a CMG$^{-URA}$ plate was used for screening, the obtained transformant strain was cultivated into YPAD liquid culture, and the chromosome DNA was extracted and used as a template to carry out PCR identification, where the primer pair was forward and reverse primers P7 and P8 of which the sequences are shown in SEQ ID No. 7 and SEQ ID No. 8 in Table 2, the predicted PCR product from successfully integrated URA3-gene-containing transformant was 2592 bp long, and the control strain PCR product was 2299 bp long. The positive transformant strain was named W303-1A (tpk2Δ::URA3).

The cells grown on the strain W303-1A (tpk2Δ::URA3) plate were further spreaded on a 5'-FOA plate, thereby screening out a colony in which the URA3 fragment was ejected by homologous recombination between two identical sequences (TPK2t) integrated on the chromosome. The same primer pair P7 and P8 was used to verify that the PCR product of the target strain in which the URA3 was successfully ejected was 1053 bp long, and the PCR fragment of the host strain W303-1A (tpk2Δ::URA3) in which the URA3 was not ejected was 2592 bp long. The 1053 bp PCR product was sequenced and the sequencing results confirmed that the expected changes occurred: 2 bases before the initiation codon of the TPK2 gene, the entire ORF region, and 107 bases after the stop codon were completely deleted. Thus, the positive transformant strain W303-1A(tpk2Δ) in which the TPK2 gene was deleted and the URA3 gene was ejected was finally obtained.

Example 2: Construction of TPK1 or TPK3 Gene-Deleted Yeast Strain

1. Construction of W303-1A (tpk1Δ)

Construction of the plasmid pUC18-TPK1p-TPK1t-URA3-TPK1t for TPK1 gene deletion: the plasmid pUC18-TPK1p-TPK1t-URA3-TPK1t was constructed based on the (1) pUC18-URA3 plasmid in Example 1 by a process identical to the process for obtaining pUC18-TPK2p-TPK2t-URA3-TPK2t by steps (2), (3) and (4) in Example 1. When the primer pair forward and reverse primers P9 and P10 of which the sequences are shown in SEQ ID No. 9 and SEQ ID No. 10 in Table 2 were used to amplify TPK1t, the product was 516 bp long; and when the primer pair forward and reverse primers P11 and P12 of which the sequences are shown in SEQ ID No. 11 and SEQ ID No. 12 in Table 2 were used for amplifying TPK1p, the product was 572 bp long.

The plasmid pUC18-TPK1p-TPK1 t-URA3-TPK1t was digested with Sac I and Psi I to obtain a linearized DNA fragment TPK1p-TPK1t-URA3-TPK1t; and the W303-1A strain competent cells were transformed, a uracil (URA) auxotrophic selectable marker was used for screening, that is, a CMG$^{-URA}$ plate was used for screening, and the obtained transformant strain was further cultivated and the chromosome was extracted as a template for PCR identification, where the primer pair was forward and reverse primers P13 and P14 of which the sequences are shown in SEQ ID No. 13 and SEQ ID No. 14 in Table 2, the successfully integrated transformant PCR product was 2631 bp long, and the control strain PCR product was 2476 bp long. The positive transformant strain was named W303-1A (tpk1Δ::URA3).

The cells grown on the strain W303-1A(tpk1Δ::UR3) plate were further spreaded on a 5'-FOA plate, thereby screening out a colony in which the URA3 fragment was ejected by homologous recombination between two identical sequences (TPK1t) integrated on the chromosome. The same primer pair P13 and P14 was used to verify that the PCR product of the target strain in which the URA3 was successfully ejected was 1102 bp long, and the control PCR fragment in which the (URA3 was not ejected was 2631 bp long. The 1102 bp PCR product was sequenced and the sequencing results confirmed that the expected changes occurred: the 70 bases before the initiation codon of the TPK1 gene, the entire ORF region, and 116 bases after the stop codon were completely deleted. Thus, the positive transformant strain W303-1A (tpk1Δ) in which the TPK1 gene was deleted and the URA3 gene was ejected was finally obtained.

II. Construction of W303-1A (tpk3Δ)

Construction of plasmid for TPK3 gene deletion: the plasmid pUC18-TPK3p-TPK3t-URA3-TPK3t was constructed based on the (1) pUC18-URA3 plasmid in Example 1 by a process identical to the process for obtaining pUC18-TPK2p-TPK2t-URA3-TPK2t by steps (2), (3) and (4) in Example 1. When the primer pair forward and reverse primers P15 and P16 of which the sequences are shown in SEQ ID No. 15 and SEQ ID No. 16 in Table 2 was used to amplify TPK3t, the product was 566 bp long; and when the primer pair forward and reverse primers P17 and P18 of which the sequences are shown in SEQ ID No. 17 and SEQ ID No. 18 in Table 2 was used to amplify TPK3p, the product was 545 bp long.

The plasmid pUC18-TPK3p-TPK3t-URA3-TPK3t was digested with Sac I and Pst I to obtain a linearized DNA fragment TPK3p-TPK3t-URA3-TPK3t; and the W303-1A strain competent cells were transformed, and screening and identification were carried out by the method identical to "construction of W303-1A (tpk2Δ))" in Example 1 to obtain the W303-1A (tpk3Δ::URA3) strain and W303-1A (tpk3Δ) strain. The primer pair used in the PCR identification was forward and reverse primers P19 and P20 of which the sequences are shown in SEQ ID No. 19 and SEQ ID No. 20 in Table 2, the successfully integrated URA3-gene-containing transformant PCR product was 2695 bp long, the successfully integrated transformant PCR product in which the URA3 gene was ejected was 1116 bp long, and the control strain PCR product was 2400 bp long. The 1116 bp PCR product was sequenced and the sequencing results confirmed that the expected changes occurred: the entire ORF region of TPK3 gene and 93 bases after the stop codon were completely deleted. Thus, the positive transformant strain W303-1A (tpk3Δ) in which the TPK3 gene was deleted and the UR43 gene was ejected was finally obtained.

Example 3: Construction of YAK1 Gene-Deleted Yeast Strain

Construction of plasmid for YAK1 gene deletion: the plasmid pUC18-YAK1p-YAK1t-URA3-YAK1t was constructed based on the (1) pUC18-URA3 plasmid in Example 1 by a process identical to the process for obtaining pUC18-TPK1p-TPK1t-URA3-TPK1t by steps (2), (3) and (4) in Example 1. When the primer pair forward and reverse primers P21 and P22 of which the sequences are shown in SEQ ID No. 21 and SEQ ID No. 22 in Table 2 was used to amplify YAK1t, the product was 506 bp long; and when the primer pair forward and reverse primers P23 and P24 of which the sequences are shown in SEQ ID No. 23 and SEQ ID No. 24 in Table 2 was used to amplify YAK p, the product was 504 bp long.

Construction of YAK1 gene-deleted strain: the plasmid pUC18-YAK1p-YAK1t-URA3-YAK1t was digested with Sac I and Pst I to obtain a linearized DNA fragment YAK1p-YAK1t-URA3-YAK1t; and the W303-1A strain competent cells were transformed, and screening and identification were carried out by the method identical to "construction of W303-1A (tpk2Δ)" in Example 1 to obtain the W303-1A (yak1Δ::URA3) strain and W303-1A (yak1Δ) strain. The primer pair used in the PCR identification was forward and reverse primers P25 and P26 of which the sequences are shown in SEQ ID No. 25 and SEQ ID No. 26 in Table 2, the successfully integrated URA3-gene-containing transformant PCR product was 2529 bp long, the successfully integrated transformant PCR product in which the URA3 gene was ejected was 1010 bp long, and the control strain PCR product was 3614 bp long. The 1010 bp PCR product was sequenced and the sequencing results confirmed that the expected changes occurred: the 40 bases before the initiation codon of the TPK1 gene, the entire ORF region, and 146 bases after the stop codon were completely deleted. Thus, the positive transformant strain W303-1A (yak1Δ) in which the YAK1 gene was deleted and the URA3 gene was ejected was finally obtained.

Example 4: Construction of Yeast Strain in which TPK1, TPK2, TPK3 and YAK1 Genes are Deleted Simultaneously The following four steps were performed to obtain a strain in which four genes were simultaneously deleted. In fact, it is known to those skilled in the art that except for the inactivation of a combination of TPK1, TPK2 and TPK3 in a haploid yeast cell (this combination cannot survive due to growth defect), the above-mentioned four genes may be modified in any order and in any combination.

1. Deletion of YAK1 Gene

The W303-1A (yak1Δ) strain was constructed by the same method as in Example 3.

II. Deletion of YAK1 and TPK1 Genes

The plasmid pUC18-TPK1p-TPK1t-URA3-TPK1t for deletion constructed in Example 2 was digested with Sac I and Pst I to obtain a linearized DNA fragment TPK1p-TPK1t-URA3-TPK1t; and the W303-1A (yak1Δ) strain competent cells in step 1 were transformed, a uracil (URA) auxotrophic selectable marker was used for screening, that is, a CMG$^{-URA}$ plate was used for screening, the obtained transformant strain was identified by the method identical to that in Example 2 to obtain the TPK1-deleted W303-1A (yak1Δ) (tpk1Δ::URA3), and further reverse screening was carried out to obtain the W303-1A (yak1Δ) (tpk1Δ).

III. Deletion of TPK2 and TPK3 Genes

The W303-1A was subjected to mating type transformation to obtain the W303-1B strain MATα leu2-3,112 ura3-1 trp1-92 his3-11,15 ade2-1 can1-100) having the identical genotype as the W303-1A strain other than mating type, and by using the W303-1B as the host, the two genes TPK2 and TPK3 were sequentially knocked out.

The plasmid pUC18-TPK2p-TPK2t-URA3-TPK2t constructed in Example 1 was digested with Sac I and Pst I to obtain a linearized DNA fragment TPK2p-TPK2t-URA3-TPK2t; and the W303-1B strain competent cells were transformed, and screening and identification were carried out by the method identical to "construction of W303-1A (tpk2Δ)" in Example 1 to obtain the W303-1B (tpk2Δ::URA3) and W303-1B (tpk2Δ) strain.

The plasmid pUC18-TPK3p-TPK3t-UR43-TPK3t constructed in Example 2 was digested with Sac I and Pst I to obtain a linearized DNA fragment TPK3p-TPK3t-URA3-TPK3t; and the W303-1B (tpk2Δ) strain competent cells were transformed, and screening and identification were carried out by the method identical to "construction of W303-1A (tpk2Δ)" in Example 1 to obtain the W303-1B (tpk2Δ tpk3Δ::URA3) strain and W303-1B (tpk2Δ tpk3Δ) strain.

IV. Simultaneous Deletion of TPK1, TPK2, TPK3 and YAK1 Genes

The W303-1A (tpk1A yak1Δ) strain was crossed with the W303-1B (tpk2Δ tpk3Δ) strain to obtain a diploid strain, then the alleles were isolated by spore production and spore isolation, and screening and identification were carried out to obtain the W303-1A (tpk1A tpk2Δ tpk3A yak1Δ) and W303-1B (tpk1A tpk2Δ tpk3A yak1Δ). Primers for the identification of four gene knockouts were the same as before. The sequencing results of the identified PCR products confirmed that the four gene nucleic acid sequences on the chromosomes of the two strains had the expected changes, and the ORF regions of both were deleted.

V. Evaluation on Growth and Fermentation Production of Extracellular cAMP of Four-Gene-Deleted Strain The four-gene-deleted strain was subjected to evaluation on growth and fermentation production of extracellular cAMP, and the operations are as follows:

1. Seed cultivation: the colony grown on the YPAD plate was picked and inoculated into a test tube containing 5 mL of YPAD medium, and cultured at 30° C., 220 rpm overnight, and if necessary, subjected to secondary inoculation and cultivation;

2. Fermentation: fermentation medium: yeast extract 10 g/L, peptone 20 g/L, and glucose 20 g/L, natural pH; the fresh seed solution was inoculated into a 100 ml flask containing 25 ml of fermentation medium, and fermented at 30° C., 220 rpm while controlling the initial OD600 value at 0.1 or so;

3. Detection of OD600 of fermentation broth: OD600 was determined to detect growth after the fermentation sample was properly diluted;

4. HPLC analysis of cAMP concentration in fermentation supernatant, i.e., extracellular cAMP concentration: the method for HPLC analysis of cAMP was adjusted according to the method of the Pharmacopoeia of the People's Republic of China: 2010 Edition (edited by the National Pharmacopoeia Commission) on page 419. The specific operations are as follows: 1) the fermentation sample was centrifuged at 13000 rpm for 1 min, the supernatant was properly diluted and filtered with a filter membrane with a pore size of 0.22 μm, and the filtrate was used for chromatographic detection: detection wavelength 258 nm, Thermo Syncronis C18 Column, mobile phase (5.78 g/L KH2PO4, 2.72 g/L tetrabutylammonium bromide): acetonitrile=85:15 ( ), pH adjusted to 4.3 with phosphoric acid, flow rate 1 mL/min, column temperature 35° C.; 2) preparation of cAMP standard sample and determination of standard curve: a cAMP standard sample was prepared into a 50 mmol/L with sterilized deionized water, and then diluted with deionized water to obtain the standard samples with final concentrations of 1, 3, 5, 7.5 and 10 μmol/L, the standard samples were filtered through a 0.2 μm filter membrane and subjected to HPLC analysis, and a peak area-cAMP concentration standard curve was made; and 3) the cAMP concentration in the fermentation broth sample was calculated by the external standard method using the standard curve.

The results of evaluation on growth and fermentation production of extracellular cAMP within 96 h are shown in Table 3.

TABLE 3

Evaluation on growth and cAMP production of four-gene-deleted strains

| Strain Name | Maximum OD$_{600}$ | Maximum Extracellular cAMP Concentration (μmol/L) |
|---|---|---|
| W303-1A | 21.1 (48 h) | 1.39 (60 h) |
| W303-1A(tpk1Δ tpk2Δ tpk3Δ yak1Δ) | 35.0 (48 h) | 200.2 (24 h) |
| W303-1B(tpk1Δ tpk2Δ tpk3Δ yak1Δ) | 33.5 (48 h) | 215.6 (24 h) |

As can be seen from Table 3, the maximum extracellular cAMP concentration by the two deleted strains were 144.0 and 155.1 times the maximum extracellular cAMP concentration by the control strain W303-1A, respectively. It should be noted that the cAMP concentration by the two deleted strains increased rapidly within 0-24 hand decreased slightly after reaching the maximum value at 24h, but remained above 180 μmol/L or above until 96h.

Example 5: Construction of Yeast Strain in which TPK1, TPK2, TPK3, YAK1 and PDE1 Genes are Deleted Simultaneously I. Deletion of PDE1 Gene PCR was carried out by using the W303-1A chromosome as a template to amplify the terminator region of PDE1 gene (abbreviated as PDE1t). The forward and reverse primers P27 and P28 of which the sequences are shown in SEQ ID No. 27 and SEQ ID No. 28 in Table 2, and Fast Pfu polymerase produced by TransGen were used, the condition was annealed at 50° C. for 1 min and extended at 72° C. for 0.5 min for a total of 32 cycles to obtain a 500 bp PCR fragment. This fragment and the vector plasmid pUC18-URA3 were digested by restriction enzymes KpnI and BamHI, ligated with a T4 DNA ligase and then E. coli Top 10 competent cells were transformed. The transformant plasmid was extracted for restriction enzyme analysis and proved to obtain the target plasmid pUC18-PDE1t-URA3.

PCR was carried out by using the W303-1A chromosome as a template to amplify the promoter region of PDE1 gene (abbreviated as PDE1p). The forward and reverse primers P29 and P30 of which the sequences are shown in SEQ ID No. 29 and SEQ ID No. 30 in Table 2, and Fast Pfu polymerase produced by TransGen were used. PCR was annealed at 50° C. for 1 min and extended at 72° C. for 0.5 min for a total of 32 cycles to obtain a 544 bp PCR fragment. This fragment and the vector plasmid pUC18-PDE1t-URA3 were digested by restriction enzymes Sac I and Kpn I and ligated with a T4 DNA ligase, then E. coli Top 10 competent cells were transformed. The transformant plasmid was extracted for restriction enzyme analysis and proved to obtain the plasmid pUC18-PDE1p-PDE1t-URA3.

The above amplified PCR product containing the PDE1t sequence was digested with Sal I and Pst I, and ligated with the same double-digested pUC18-PDE1p-PDE1t-URA3 large fragment to obtain the plasmid pUC18-PDE1p-PDE1t-URA3-PDE 1t.

The plasmid pUC18-PDE1p-PDE1t-URA3-PDE It was digested with double enzymes Sac I and Pst I, and the W303-1A (tpk1Δ tpk2Δ tpk3Δ yak1Δ) constructed in Example 4 was used as a host to construct the W303-1A (tpk1Δ tpk2Δ tpk3Δ yak1Δ pde1Δ::URA3) and W303-1A (tpk1Δ tpk2Δ tpk3Δ yak1Δ pde1Δ) by using the method identical to that in "construction of W303-1A (tpk2Δ) strain" in Example 1. The primer pair used in the PCR identification was forward and reverse primers P31 and P32 of which the sequences are shown in SEQ ID No. 31 and SEQ ID No. 32 in Table 2, the successfully integrated URA3-gene-containing transformant PCR product was 2958 bp long, the successfully integrated transformant PCR product in which the URA3 gene was ejected was 1445 bp long, and the control strain PCR product was 2635 bp long. The 1445 bp PCR product was sequenced and the sequencing results confirmed that the expected changes occurred: the 40 bases before the initiation codon of the PDE1 gene, the entire ORF region, and 46 bases after the stop codon were completely deleted. Thus, the positive transformant strain in which the PDE1 gene was deleted and the URA3 gene was ejected was finally obtained.

II. Comparison of cAMP Production with W303-1A (tpk1Δ tpk2Δ tpk3Δ yak1Δ pde1Δ::URA3) and W303-1A (tpk1Δtpk2Δ tpk3Δ yak1Δ pde1Δ)

To compare the possible effects of the selectable marker gene URA3 on cAMP production, a preliminary evaluation on cAMP production with two strains was performed. 1. Seed cultivation: same as in Example 4; 2. Fermentation: 1) fermentation medium: yeast extract 10 g/L, peptone 20 g/L, and glucose 20 g/L, natural pH; and 2) fermentation condition: the fresh seed was inoculated into a 100 ml flask containing 25 ml of fermentation medium, and fermented at 30° C., 220 rpm while controlling the initial OD600 value at 0.1 or so. The analysis of the fermentation broth was the same as the HPLC analysis method in Example 4. The results of extracellular cAMP production within 120 h are shown in FIG. 2. The results in FIG. 2 show that: 1. the maximum extracellular cAMP concentrations within 120 h by the two deleted strains were 252.0 and 953.8 μmol/L, respectively, which were 173.8 and 657.8 times that of the control strain W303-1A (1.45 μmol/L), and 1.17 and 4.42 times that of W303-1B (tpk1Δ tpk2Δ tpk3Δ yak1Δ) strain in Example 4, respectively; 2. The cAMP concentration by the strain W303-1A (tpk1Δ tpk2Δ tpk3Δ yak1Δ pde1Δ::URA3) was basically stable from 48 h, while the cAMP concentration by W303-1A (tpk1Δtpk2Δtpk3Δyak1Δpde1Δ) increased continuously; and 3. No retaining URA3 gene can significantly increase the cAMP yield.

III. Evaluation on Growth and cAMP Production of W303-1A (tpk1Δ tpk2Δ tpk3Δ yak1Δ pde1Δ)

The URA3-free five-gene-deleted strain was subjected to evaluation on growth and fermentation production of extracellular cAMP: 1. The seed cultivation: same as in Example 4; 2. fermentation: 1) fermentation medium: yeast extract 10 g/L, peptone 20 g/L, and glucose 20-150 g/L, natural pH; and 2) fermentation conditions: the fresh seed solution was inoculated into a 100 ml flask containing 25 ml of fermentation medium, and fermented at 30° C., 220 rpm while controlling the initial OD600 value at 1 or so. The analysis of the fermentation broth was the same as the HPLC analysis method in Example 4. The results of evaluation on growth and fermentation production of extracellular cAMP within 120 h are shown in Table 4.

TABLE 4

Evaluation on growth and cAMP production of five-gene-deleted strains

| Glucose Concentration (g/L) | Maximum $OD_{600}$ | Maximum Extracellular cAMP Concentration (μmol/L) |
|---|---|---|
| 20 | 31.1 (24 h) | 981.0 (48 h) |
| 50 | 35.0 (48 h) | 2223.7 (72 h) |
| 100 | 63.7 (72 h) | 3596.6 (96 h) |
| 150 | 69.5 (72 h) | 3925.6 (96 h) |

Example 6: BAS1-BAS2 Fusion Co-Expression

The BAS1 and BAS2 genes were subjected to fusion co-expression and integrated into the chromosome of the yeast cell. Therefore, the construction of a fusion co-expression integration vector with left and right homology arms is firstly required. The integration site selected here is YNRC Δ 9, which was reported to have high gene expression efficiency in the literature (Bai Flagfeldt D, Siewers V, Huang L. et al. Characterization of chromosomal integration sites for heterologous gene expression in Saccharomyces cerevisiae. Yeast, 2009, 26(10): 545-551), and is located on chromosome XIV.

Figure 3:
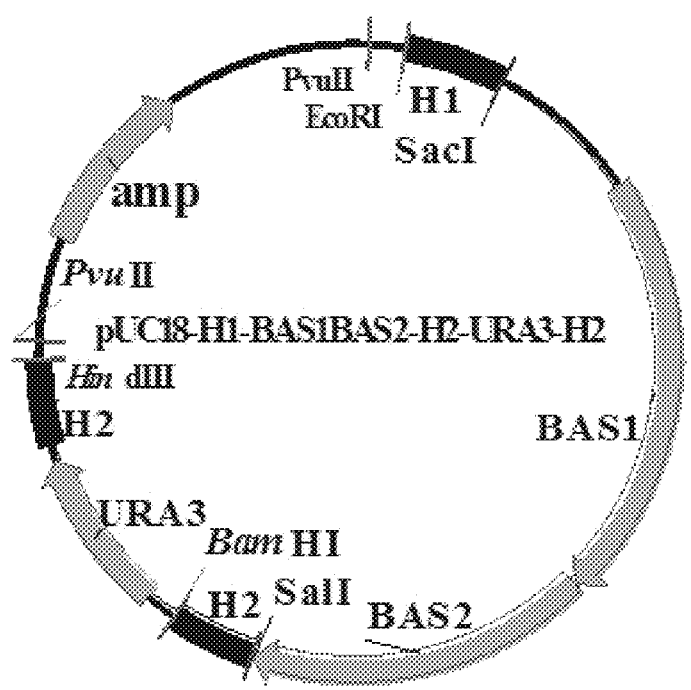
FIG. 3 is a schematic diagram of the plasmid pUC18-H1$_{YNRCA9}$-BAS1-BAS2-H2$_{YNRCA9}$-URA3-H2$_{YNRCA}$ according to example 6.

I. Construction of BAS1-BAS2 Fusion Co-Expression Plasmid 4 ligations were performed to obtain the BAS1-BAS2 fusion co-expression plasmid pUC18-H1$_{YNRCΔ9}$-BAS1-BAS2-H2$_{YNRCΔ9}$-URA3-H2$_{YNCΔ9}$ (see FIG. 3 for the schematic diagram).

1. Construction of pUC18-H1$_{YNRCΔ9}$-SacI-SalI-H2$_{YNRCΔ9}$ Plasmid

PCR was performed by using the strain W303-1A chromosomal DNA as a template to amplify the partial sequence of YNRCΔ9 to obtain the integrated left and right homology arms. The forward and reverse primers P33 and P34 of which the sequences are shown in SEQ ID No. 33 and SEQ ID No. 34 in Table 2, and the Fast Pfu polymerase produced by TransGen were used, PCR was annealed at 50° C. for 1 min and extended at 72° C. for 45 sec for a total of 32 cycles to obtain a 521 bp PCR1 fragment (the corresponding sequence was used as the integrated left homology arm H1YNRCΔ9). The forward and reverse primers P35 and P36 of which the sequences are shown in SEQ ID No. 35 and SEQ ID No. 36 in Table 2 were used, and the same method was used to obtain a 448 bp PCR2 fragment (the corresponding sequence was used as the integrated right homology arm H2YNRCΔ9). By using PCR1 and PCR2 products as the templates and P33 and P36 as the primer pair, the overlapping extension PCR was performed to obtain a 949 bp PCR12 fragment. The restriction enzyme cutting site EcoRI was added to the 5' end of this fragment, BamHI was added to the 3' end, and SacI and Sal I were added in the middle. The PCR product was digested with EcoRI and BamHI and ligated with the same double-digested pUC18 large fragment. E. coli Top 10 competent cells were transformed, and the transformant plasmid was extracted to perform digestion identification and proved to obtain the plasmid pUC18-H1YNRCΔ9-SacI-SalI-H2 YNRCΔ9. The sequencing results proved that the cloned fragment did not undergo mutation.

2. Construction of pUC18-H1$_{YNRCΔ9}$-SacI-SalI-H2$_{YNRCΔ9}$-URA3-H2$_{YNRCΔ9}$ Plasmid PCR was performed to amplify the URA3 gene by using YCplac33 as the template to obtain the selectable marker gene for integration. The forward and reverse primers P37 and P38 of which the sequences are shown in SEQ ID No. 37 and SEQ ID No. 38 in Table 2, and Fast Pfu polymerase produced by TransGen were used, and PCR was annealed at 50° C. for 1 min and extended at 72° C. for 1 min for a total of 32 cycles to obtain a 1060 bp PCR1 fragment. PCR was performed by still using the W303-1A chromosomal DNA as the template to amplify the H2 YNRC Δ 9 fragment while the forward and reverse primer pair was replaced with P39 and P40 of which the sequences are SEQ ID No. 39 and SEQ ID No. 40 in Table 2, to obtain a 438 bp PCR2 fragment. By using PCR1 and PCR2 products as the templates and P37 and P40 as the primer pair, the overlapping extension PCR was performed to obtain a 1478 bp PCR12 fragment. The restriction enzyme cutting site BamHI was added to the 5' end of this fragment, and HindIII was added to the 3' end. The PCR product was digested with BamHI and HindIII and ligated with the same double-digested pUC18-H1$_{YNRCΔ9}$-SacI-SalI-H2$_{YNRCΔ9}$ large fragment. E. coli Top 10 competent cells were transformed, and the transformant plasmid was extracted to perform digestion identification and proved to obtain the plasmid pUC18-H1$_{YNRCΔ9}$-SacI-SalI-H2$_{YNRCΔ9}$-URA3-H2$_{YNRCΔ9}$. The sequencing results proved that the cloned fragment did not undergo mutation.

3. Construction of pGEM-T Easy-BAS1-BAS2 Plasmid

PCR was carried out by using the W303-1A chromosomal DNA as a template to amplify the gene BAS1. The forward and reverse primers P41 and P42 of which the sequences are shown in SEQ ID No. 41 and SEQ ID No. 42 in Table 2 and Fast Pfu polymerase produced by TransGen were used, PCR was annealed at 50° C. for 1 min and extended at 72° C. for 2.5 min for a total of 32 cycles to obtain a 2907 bp PCR1 fragment. The restriction enzyme cutting site SacI was added to the 5' end of this fragment, including the 762 bp sequence upstream of the ATG of the BAS 1 gene initiation codon and the 2112 bp ORF sequence including ATG, and deleting a 324 bp (including the stop codon) sequence at the 3' end.

PCR was carried out by using the W303-1A chromosomal DNA as a template to amplify the gene BAS2. The forward and reverse primers P43 and P44 of which the sequences are shown in SEQ ID No. 43 and SEQ ID No. 44 in Table 2, and Fast Pfu polymerase produced by TransGen were used, PCR was annealed at 50° C. for 1 min and extended at 72° C. for 1.5 min for a total of 32 cycles to obtain a 1692 bp PCR2 fragment. The restriction enzyme cutting site Sal I was added to the 3' end, including all sequences of the BAS2 gene ORF (including the stop codon).

By using PCR1 and PCR2 products as the templates and P41 and P44 as the primer pair, the overlapping extension PCR was performed to obtain a 4578 bp PCR12 fragment. Then the PCR fragment was added to the ends with base adenine, separated and recovered by agarose gel electrophoresis. Such PCR fragment was ligated to a pGEM-T easy vector purchased from Promega according to the instructions, E. coli Top 10 competent cells were transformed, and the transformant plasmid was extracted to carry out digestion identification and proved to obtain the plasmid pGEM-T easy-BAS1-BAS2. The sequencing results proved that the cloned fragment did not undergo mutation.

4. Construction of pUC18-H1$_{YNRCΔ9}$-BAS1-BAS2-H2$_{YNRCΔ9}$-URA3-H2$_{YNRCΔ9}$ plasmid The pGEM-T easy-BAS1-BAS2 was digested with SacI and Sal I, and ligated with the same double-digested pUC18-H1$_{YNRCΔ9}$-SacI-SalI-H2$_{YNRCΔ9}$-URA3-H2$_{YNRCΔ9}$ large fragment after the large fragment SacI-BAS1-BAS2-Sal I was recovered, to obtain the integrated plasmid pUC18-H1$_{YNRCΔ9}$-BAS1-BAS2-H2$_{YNRCΔ9}$-URA3-H2$_{YNRCΔ9}$.

II. Construction of Strain W303-1A (tpk1Δ tpk2Δ tpk3Δ yak1Δ pde1ΔBAS1BAS2)

The plasmid pUC18-H1$_{YNRCΔ9}$-BAS1-BAS2-H2$_{YNRCΔ9}$-URA3-H2$_{YNRCΔ9}$ was digested with Pvu II to obtain a linearized DNA fragment H1$_{YNRCΔ9}$-BAS1-BAS2-H2$_{YNRCΔ9}$-URA3-H2$_{YNRCΔ9}$; and the strain W303-1A (tpk1Δ tpk2Δ tpk3Δ yak1Δ pde1Δ) competent cells were transformed, and screening and identification were carried out by the method identical to "construction of W303-1A (tpk2Δ)" in example 1 to obtain the strains W303-1A (tpk1Δ tpk2Δ tpk3Δ yak1A pde1Δ BAS1BAS2-URA3) and W303-1A (tpk1Δ tpk2Δ tpk3Δ yak1Δ pde1Δ BAS1BAS2). The forward and reverse primers P45 and P46 of which the sequences are shown in SEQ ID No. 45 and SEQ ID No. 46 in Table 2 were used in the PCR identification. The successfully integrated URA3-gene-containing transformant PCR product was 7389 bp long, the successfully integrated transformant PCR product in which the URA3 gene was ejected was 5929 bp long, and the control strain PCR product was 1687 bp long. The 5929 bp PCR product was sequenced and the results confirmed that the expected changes occurred: a 321 bp sequence of the YNRCΔ9 site was knocked out, and a BAS1BAS2 fusion fragment was inserted instead. This fragment did not undergo mutation, and did not contain the URA3 gene.

III. Evaluation on Growth and cAMP Production of Strain W303-1A(tpk1Δ tpk2Δ tpk3Δ yak1Δ pde1ΔBAS1BAS2)

Example 5 proved that the glucose concentration significantly affects the production of cAMP. In view of the components required for cAMP synthesis (the molecular formula is C10H12N5O6P), while the glucose concentration is increased, it is speculated that the contents of nitrogen and phosphorus in the medium, especially the content of nitrogen, may become the primary limiting factor for cAMP synthesis. In addition, as a precursor for cAMP synthesis, the condition of extracellular adenine also greatly affects the expression level of each gene in the purine synthesis pathway, which in turn affects cAMP production. Therefore, the cAMP production of the above strains at two yeast extract/peptone levels (1*YP, 2*YP) under the condition that adenine was added was compared here. The specific operations are as follows: 1. The seed cultivation: same as in Example 4; 2. fermentation: 1) fermentation medium: yeast extract 10 g/L, peptone 20 g/L, abbreviated as 1*YP, and glucose 150 g/L, natural pH; yeast extract 20 g/L, peptone 40 g/L, abbreviated as 2*YP, and glucose 150 g/L, natural pH; the amount of adenine added was 0.625 and 1.25 g/L, abbreviated as A0.625 and A1.25, respectively; 2) fermentation condition: the fresh seed solution was inoculated into a 100 ml flask containing 25 ml of fermentation medium, and fermented at 30° C., 220 rpm while controlling the initial OD600 value at 1 or so; 3) analysis of fermentation broth: cAMP HPLC analysis method was same as in Example 4, and additionally adenine HPLC analysis was performed as followings: a. the sample processing and HPLC analysis: same as sample processing and HPLC analysis of cAMP analysis; b. making adenine standard curve: an adenine standard sample was prepared into a 5 mg/mL with sterilized deionized water, and then diluted with deionized water to obtain the standard samples with final concentrations of 0.1, 0.2, 0.3, 0.4 and 0.5 mg/mL, respectively, the standard samples were subjected to chromatographic analysis after filtration sterilization, and a standard curve was made; and c. the concentration of adenine in the fermentation broth sample was calculated by the external standard method using the standard curve.

The fermentation results are shown in Table 5. The results in Table 5 indicate that: 1. under the fermentation conditions of 1*YP and 15% glucose, the maximum extracellular cAMP concentration by the fusion co-expression BAS1-BAS2 strain is higher than that (3925.6 μmol/L) of the strain W303-1A(tpk1Δtpk2Δtpk3Δyak1Δpde1Δ) in Example 5, the former being 1.108 times of the latter; 2. the effect on the extracellular cAMP yield by increasing concentrations of yeast powder and peptone is extremely significant; and 3. adding adenine into medium can further increase the extracellular cAMP yield.

TABLE 5

Evaluation on cAMP production of strain W303-1A (tpk1Δ tpk2Δ tpk3Δ yak1Δ pde1ΔBAS1-BAS2)

| Component | Maximum OD$_{600}$ | Maximum cAMP Concentration (μmol/L) | Ratio | Ratio |
|---|---|---|---|---|
| 1*YP, Glucose 150 g/L | 70.1 (72 h) | 4348.8 (120 h) | 1 | — |
| 2*YP, Glucose 150 g/L | 71.6 (96 h) | 8291.5 (168 h) | 1.907 | 1 |
| 2*YP, Glucose 150 g/L, A0.625 | 68.4 (120 h) | 9265.3 (168 h) | 2.131 | 1.117 |
| 2*YP, Glucose 150 g/L, A1.25 | 64.4 (120 h) | 9721.6 (168 h) | 2.235 | 1.172 |

The invention claimed is:

1. A yeast for cyclic adenosine monophosphate (cAMP) synthesis, wherein the yeast includes:
   a) first gene modifications to the protein kinase A (PKA) catalytic subunit encoding genes TPK1, TPK2 and TPK3, wherein the activity or expression of PKA is completely inhibited such that PKA-mediated feedback inhibition of cAMP synthesis is eliminated, wherein the first gene modifications inhibit the growth of the yeast;
   b) a second gene modification to the Yak1 encoding gene thereby eliminating the growth inhibition caused by the first gene modifications such that the yeast grows normally and the cAMP yield by the yeast is increased relative to the cAMP yield by an unmodified yeast;
   c) a third gene modification to the cAMP phosphodiesterase encoding gene PDE1 to reduce the degradation of cAMP, thereby increasing cAMP yield;
   and wherein the yeast does not contain a functional ura3 gene.

2. The yeast according to claim 1, wherein the activity or expression of the Yak1 is completely inhibited.

3. The yeast according to claim 2, wherein the Yak1 gene is deleted.

4. The yeast according to claim 1, wherein the activity or expression of the PDE1 is completely inhibited.

5. The yeast according to claim 4, wherein the PDE1 gene is deleted.

6. The yeast according to claim 1, wherein the PKA encoding genes TPK1, TPK2 and TPK3 are deleted.

7. The yeast according to claim 1, wherein the yeast further comprises a fourth gene modification to enhance the positive regulation of synthesis of a cAMP precursor in a purine synthesis pathway, so that the synthesis of the cAMP precursor increases, thereby increasing the cAMP yield.

8. The yeast according to claim 7, wherein the fourth gene comprises transcription factor Bas1 and Bas2 encoding genes.

9. The yeast according to claim 8, wherein the gene modification increases the expression of the Bas1/Bas2 complex.

10. The yeast according to claim 7, wherein the fourth gene modification comprises point mutation, ligation of a strong promoter, ligation of an enhancer, increase of a copy number, or fusion co-expression.

11. The yeast according to claim 1, wherein the yeast is *Saccharomyces cerevisiae*.

* * * * *

SEQUENCE LISTING

<160> NUMBER OF SEQ ID NOS: 46

<210> SEQ ID NO 1
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 1
cccgggggat ccttgattcg gtaatctccg aa                32

<210> SEQ ID NO 2
<211> LENGTH: 34
<212> TYPE: DNA

```
<213> ORGANISM: Artificial sequence
<220> FEATURE:
<223> OTHER INFORMATION: synthetic oligonucleotide:primer

<400> SEQUENCE: 2
cccggggtcg acctgatata attaaattga agct                              34

<210> SEQ ID NO 3
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 3
cccggggtcg acggtaccac ctaacggatg ccttattt                          38

<210> SEQ ID NO 4
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 4
cccgggctgc agggatccgg gattttggac cttagact                          38

<210> SEQ ID NO 5
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 5
cccggggagc tctcaatttg gttgtaagca ac                                32

<210> SEQ ID NO 6
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 6
cccgggggta cccgacaatt ttcaacagta tg                                32

<210> SEQ ID NO 7
<211> LENGTH: 20
<212> TYPE: DNA
<213> ORGANISM: Artificial sequence
<220> FEATURE:
<223> OTHER INFORMATION: synthetic oligonucleotide:primer

<400> SEQUENCE: 7
cctcaagata aaccagctgg                                              20

<210> SEQ ID NO 8
<211> LENGTH: 20
<212> TYPE: DNA
<213> ORGANISM: Artificial sequence
<220> FEATURE:
<223> OTHER INFORMATION: synthetic oligonucleotide:primer

<400> SEQUENCE: 8
ataatggtga tatcagcacc                                              20
```

<210> SEQ ID NO 9
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 9
cccggggtcg acggtaccgt tactacggag atggaacg                     38

<210> SEQ ID NO 10
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 10
cccgggctgc agggatccat ccctgaaggc ttaaatag                     38

<210> SEQ ID NO 11
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 11
cccggggagc tcctccgtta atcctagtct gt                           32

<210> SEQ ID NO 12
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 12
cccgggggta ccttctgtgc tacctttgaa gc                           32

<210> SEQ ID NO 13
<211> LENGTH: 20
<212> TYPE: DNA
<213> ORGANISM: Artificial sequence
<220> FEATURE:
<223> OTHER INFORMATION: synthetic oligonucleotide:primer

<400> SEQUENCE: 13
atccctccca tcctccttaa                                         20

<210> SEQ ID NO 14
<211> LENGTH: 20
<212> TYPE: DNA
<213> ORGANISM: Artificial sequence
<220> FEATURE:
<223> OTHER INFORMATION: synthetic oligonucleotide:primer

<400> SEQUENCE: 14
gaaggagccg cagcattatt                                         20

<210> SEQ ID NO 15
<211> LENGTH: 38
<212> TYPE: DNA
<213> ORGANISM: Artificial sequence
<220> FEATURE:

<223> OTHER INFORMATION: synthetic oligonucleotide:primer

<400> SEQUENCE: 15
cccggggtcg acggtaccga ttcttggtga gtctaaca                        38

<210> SEQ ID NO 16
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 16
cccgggctgc agggatcctg gaacgctttt ttgcttgt                        38

<210> SEQ ID NO 17
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 17
cccggggagc tcgtcaacgt ttcagatact ct                              32

<210> SEQ ID NO 18
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 18 cccggggggta cctttgtgca ggctcgctct tt                             32

<210> SEQ ID NO 19
<211> LENGTH: 22
<212> TYPE: DNA
<213> ORGANISM: Artificial sequence
<220> FEATURE:
<223> OTHER INFORMATION: synthetic oligonucleotide:primer

<400> SEQUENCE: 19
gcgactatgc attttttgcaa aa                                        22

<210> SEQ ID NO 20
<211> LENGTH: 20
<212> TYPE: DNA
<213> ORGANISM: Artificial sequence
<220> FEATURE:
<223> OTHER INFORMATION: synthetic oligonucleotide:primer

<400> SEQUENCE: 20
cggagccttc atgagataaa                                            20

<210> SEQ ID NO 21
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 21
cccggggtcg acggtaccaa agtttctgca ctagcttt                        38

<210> SEQ ID NO 22
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 22
cccgggctgc agggatccag agagaggacc catggaat                              38

<210> SEQ ID NO 23
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 23
cccggggagc tcctttcgcc ctcaaactca ac                                    32

<210> SEQ ID NO 24
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 24 cccggggggta ccatgttccc ttgcacaatg gc                                   32

<210> SEQ ID NO 25
<211> LENGTH: 21
<212> TYPE: DNA
<213> ORGANISM: Artificial sequence
<220> FEATURE:
<223> OTHER INFORMATION: synthetic oligonucleotide:primer

<400> SEQUENCE: 25
caatacggat gaatatttgt g                                                21

<210> SEQ ID NO 26
<211> LENGTH: 20
<212> TYPE: DNA
<213> ORGANISM: Artificial sequence
<220> FEATURE:
<223> OTHER INFORMATION: synthetic oligonucleotide:primer

<400> SEQUENCE: 26
acttttgatt gcgctgtgaa                                                  20

<210> SEQ ID NO 27
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 27
cccggggtcg acggtaccaa attcattacc cgggagca                              38

<210> SEQ ID NO 28
<211> LENGTH: 38
<212> TYPE: DNA
<213> ORGANISM: Artificial sequence
<220> FEATURE:
<223> OTHER INFORMATION: synthetic oligonucleotide:primer

<400> SEQUENCE: 28
cccgggctgc agggatccat gctggaaccc tcatatga                    38

<210> SEQ ID NO 29
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 29
cccggggagc tccagacata tagtctcgaa ga                          32

<210> SEQ ID NO 30
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 30 cccggggta ccctcgtta aaagccactt tc                            32

<210> SEQ ID NO 31
<211> LENGTH: 19
<212> TYPE: DNA
<213> ORGANISM: Artificial sequence
<220> FEATURE:
<223> OTHER INFORMATION: synthetic oligonucleotide:primer

<400> SEQUENCE: 31
aatcttactt tggcgaatg                                         19

<210> SEQ ID NO 32
<211> LENGTH: 21
<212> TYPE: DNA
<213> ORGANISM: Artificial sequence
<220> FEATURE:
<223> OTHER INFORMATION: synthetic oligonucleotide:primer

<400> SEQUENCE: 32
acactatttc cttgttcata c                                      21

<210> SEQ ID NO 33
<211> LENGTH: 30
<212> TYPE: DNA
<213> ORGANISM: Artificial sequence
<220> FEATURE:
<223> OTHER INFORMATION: synthetic oligonucleotide:primer

<400> SEQUENCE: 33
gcgcgcgaat tccgtattga ccattcctaa                             30

<210> SEQ ID NO 34
<211> LENGTH: 39
<212> TYPE: DNA
<213> ORGANISM: Artificial sequence
<220> FEATURE:
<223> OTHER INFORMATION: synthetic oligonucleotide:primer

<400> SEQUENCE: 34
tcgactcccg ggtaccgagc tctatcgtat cgcagccta                   39

<210> SEQ ID NO 35
<211> LENGTH: 38

```
<212> TYPE: DNA
<213> ORGANISM: Artificial sequence
<220> FEATURE:
<223> OTHER INFORMATION: synthetic oligonucleotide:primer

<400> SEQUENCE: 35
gctcggtacc cgggagtcga ctgtagacct aagttcat                              38

<210> SEQ ID NO 36
<211> LENGTH: 30
<212> TYPE: DNA
<213> ORGANISM: Artificial sequence
<220> FEATURE:
<223> OTHER INFORMATION: synthetic oligonucleotide:primer

<400> SEQUENCE: 36
atattaggat ccgccttgct tacctagatg                                       30

<210> SEQ ID NO 37
<211> LENGTH: 28
<212> TYPE: DNA
<213> ORGANISM: Artificial sequence
<220> FEATURE:
<223> OTHER INFORMATION: synthetic oligonucleotide:primer

<400> SEQUENCE: 37
gcgttaggat ccgattcggt aatctccg                                         28

<210> SEQ ID NO 38
<211> LENGTH: 26
<212> TYPE: DNA
<213> ORGANISM: Artificial sequence
<220> FEATURE:
<223> OTHER INFORMATION: synthetic oligonucleotide:primer

<400> SEQUENCE: 38
aggtctacag gggtaataac tgatat                                           26

<210> SEQ ID NO 39
<211> LENGTH: 28
<212> TYPE: DNA
<213> ORGANISM: Artificial sequence
<220> FEATURE:
<223> OTHER INFORMATION: synthetic oligonucleotide:primer

<400> SEQUENCE: 39
gttattaccc ctgtagacct aagttcat                                         28

<210> SEQ ID NO 40
<211> LENGTH: 30
<212> TYPE: DNA
<213> ORGANISM: Artificial sequence
<220> FEATURE:
<223> OTHER INFORMATION: synthetic oligonucleotide:primer

<400> SEQUENCE: 40
cgtacgaagc ttgccttgct tacctagatg                                       30

<210> SEQ ID NO 41
<211> LENGTH: 32
<212> TYPE: DNA
<213> ORGANISM: Artificial sequence
<220> FEATURE:
<223> OTHER INFORMATION: synthetic oligonucleotide:primer

<400> SEQUENCE: 41
```

```
gggcccgagc tctctttagc cgtaattgcg aa                                    32

<210> SEQ ID NO 42
<211> LENGTH: 42
<212> TYPE: DNA
<213> ORGANISM: Artificial sequence
<220> FEATURE:
<223> OTHER INFORMATION: synthetic oligonucleotide:primer

<400> SEQUENCE: 42
gtacgagaat tcttccatca tggatgtagt ccttgatatc tc                         42

<210> SEQ ID NO 43
<211> LENGTH: 21
<212> TYPE: DNA
<213> ORGANISM: Artificial sequence
<220> FEATURE:
<223> OTHER INFORMATION: synthetic oligonucleotide:primer

<400> SEQUENCE: 43
atgatggaag aattctcgta c                                                21

<210> SEQ ID NO 44
<211> LENGTH: 33
<212> TYPE: DNA
<213> ORGANISM: Artificial sequence
<220> FEATURE:
<223> OTHER INFORMATION: synthetic oligonucleotide:primer

<400> SEQUENCE: 44
gggcccgtcg actcatatcc atctatgctc gtc                                   33

<210> SEQ ID NO 45
<211> LENGTH: 19
<212> TYPE: DNA
<213> ORGANISM: Artificial sequence
<220> FEATURE:
<223> OTHER INFORMATION: synthetic oligonucleotide:primer

<400> SEQUENCE: 45
tcaactttgg gattactgc                                                   19

<210> SEQ ID NO 46
<211> LENGTH: 19
<212> TYPE: DNA
<213> ORGANISM: Artificial sequence
<220> FEATURE:
<223> OTHER INFORMATION: synthetic oligonucleotide:primer

<400> SEQUENCE: 46
ctcatcattt gcgtcatct                                                   19
```